United States Patent
Cantor et al.

(10) Patent No.: US 6,312,715 B1
(45) Date of Patent: *Nov. 6, 2001

(54) ADHESIVE MICROSPHERE DRUG DELIVERY COMPOSITION

(75) Inventors: Adam S. Cantor, St. Paul; Hye-ok Choi, Woodbury; Joaquin Delgado, St. Paul; Chan U. Ko, Arcadia; Thu-Van Tran, Maplewood, all of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/071,667

(22) Filed: May 1, 1998

(51) Int. Cl.[7] .............................. A61F 13/02; A61F 13/00; A61L 15/16; A61K 9/70; A61K 9/14
(52) U.S. Cl. ........................... 424/448; 424/449; 424/487
(58) Field of Search ..................................... 424/487, 448, 424/449

(56) References Cited

U.S. PATENT DOCUMENTS

| | | |
|---|---|---|
| 3,598,123 * | 8/1971 | Zaffaroni .............................. 424/448 |
| 3,691,140 | 9/1972 | Silver . |
| 4,166,152 | 8/1979 | Baker et al. . |
| 4,495,318 | 1/1985 | Howard . |
| 4,689,338 | 8/1987 | Gerster . |
| 4,737,559 | 4/1988 | Kellen et al. . |
| 4,786,696 | 11/1988 | Bohnel . |
| 4,968,562 | 11/1990 | Delgado . |
| 4,988,467 | 1/1991 | Holdsworth et al. . |
| 5,045,569 | 9/1991 | Delgado . |
| 5,053,436 | 10/1991 | Delgado . |
| 5,223,261 * | 6/1993 | Nelson et al. ....................... 424/443 |
| 5,494,680 | 2/1996 | Peterson . |
| 5,508,313 | 4/1996 | Delgado et al. . |
| 5,571,617 | 11/1996 | Cooprider et al. . |
| 5,614,310 | 3/1997 | Delgado et al. . |
| 5,882,675 | 3/1999 | Ninomiya et al. ................... 424/448 |

FOREIGN PATENT DOCUMENTS

| | | |
|---|---|---|
| 793972 | 9/1997 | (EP) . |
| 58-12255 | 3/1983 | (JP) . |
| 96/01280 | 1/1996 | (WO) . |
| 97/46633 | 12/1997 | (WO) . |
| 97/46634 | 12/1997 | (WO) . |

* cited by examiner

Primary Examiner—Thurman K. Page
Assistant Examiner—Todd D Ware
(74) Attorney, Agent, or Firm—MarySusan Howard; Ted K. Ringsred; Robert W. Sprague

(57) ABSTRACT

Transdermal drug delivery compositions comprising pressure sensitive adhesive microspheres that contain a softening agent and/or a drug. Typically the microspheres contain at least 10 wt-% of a softening agent. The drug and/or softening agent can be incorporated into the microspheres during or after their formation.

22 Claims, No Drawings

ADHESIVE MICROSPHERE DRUG DELIVERY COMPOSITION

FIELD OF THE INVENTION

This invention relates to transdermal drug delivery compositions that contain pressure sensitive adhesive microspheres containing a softening agent and/or a therapeutic agent. The invention additionally relates to an in-situ method of preparing pressure sensitive adhesive microspheres that contain a softening agent and/or a therapeutic agent.

BACKGROUND OF THE INVENTION

Inherently tacky pressure sensitive adhesive microspheres are known in the art to be useful in repositionable pressure sensitive adhesive applications and there are numerous references discussing the preparation and/or use of inherently tacky, elastomeric polymeric microspheres. Pressure sensitive adhesive microspheres may be solid or hollow and are generally crosslinked to an extent such that the particulate nature of the adhesive is maintained throughout processing and use. Typically, pressure sensitive adhesive microspheres are prepared via suspension polymerization of one or more free radically polymerizable monomers in the presence of surfactants and/or suspension stabilizers. Choice of surfactants and/or suspension stabilizers and their specific combinations with specific monomers can determine suspension stability, desired particle morphology, performance characteristics, and the like.

Various copolymerizable monomeric components have been added to the free radically polymerizable monomers, suspension stabilizers and/or surfactants to modify the adhesive properties of these suspension polymerized microspheres. For example, nitrogen-containing polar monomers have been added to acid-free acrylate suspension polymerization mixtures to form adhesive microspheres containing multiple internal voids. Polar comonomers having no dissociable protons or low levels of dissociable protons, when used along with particular surfactant and polymeric stabilizer combinations, can be added to suspension polymerizable formulations to yield adhesive microspheres having enhanced adhesive properties while maintaining their repositionable and self cleaning qualities against a variety of surfaces.

Copolymerizable or otherwise incorporated oligomeric and polymeric additives have also been employed in suspension polymerized adhesive microspheres to alter microsphere adhesive properties and other performance characteristics. Hydrophilic oligomers and polymers have been included in suspension polymerizable adhesive microsphere formulations to provide improved microsphere stability and, in some formulations, water dispersibility. Water insoluble polymeric components have also been incorporated into adhesive microspheres by suspension polymerization of alkyl(meth)acrylate and other comonomers in the presence of such polymeric components. This method of incorporation allows for the inclusion of water insoluble polymer components into adhesive microspheres that could not typically be incorporated under standard free radical suspension polymerization conditions. Another advantage of this water insoluble polymer incorporation is to modify the physical and adhesive properties of the microspheres. Finally, crystalline polymers or crystallizable monomers have also been added during suspension polymerization to provide adhesive microspheres having thermally controllable shape memory.

Drugs and other therapeutically active agents have been administered transdermally or percutaneously using a variety of methods and devices. One known method is to incorporate the drug into a continuous adhesive matrix, either alone or in combination with one or more excipients that enhance the delivery of drug across the skin. Examples of such systems are found, for example in Nelson et al., U.S. Pat. No. 5,223,261 and Peterson, U.S. Pat. No. 5,494,680.

There have been some attempts in the prior art to develop transdernal drug delivery systems that use pressure sensitive adhesive particles in place of a continuous adhesive matrix. For example, JP 58-12255 describes an adhesive tape or sheet made up of acrylic polymer particles that contain a drug such as a steroid. EP 793,972 describes a transdermal drug delivery device that contains finely pulverized acrylate adhesive particles in combination with a drug.

SUMMARY OF THE INVENTION

The transdermal drug delivery composition of the present invention comprises pressure sensitive adhesive microspheres comprising (a) at least 10 wt-% of a softening agent incorporated within the microspheres and optionally comprising (b) a therapeutically effective amount of a drug.

The use of polymeric microspheres as described herein provides a high degree of flexibility in formulating transdermal drug delivery compositions. In particular, the transdermal drug delivery compositions of the invention can tolerate the inclusion of a relatively large amount of a softening agent without undue loss of cohesive strength. This tolerance for softening agents or excipients allows one to achieve excellent delivery of drug through the skin without sacrificing adhesive properties.

The invention also provides a transdermal drug delivery device comprising a transdermal drug delivery composition comprised of pressure sensitive adhesive microspheres comprising (a) at least 10 wt-% of a softening agent incorporated within the microspheres and optionally comprising (b) a therapeutically effective amount of a drug disposed upon a backing.

Another aspect of the invention provides a method of preparing a transdermal drug delivery composition comprising the steps of:

a) forming an oil phase comprising one or more acrylic acid ester, methacrylic acid ester, or vinyl ester monomers alone or in any combination; a non-reactive, oil soluble softening agent and/or drug; and an oil soluble free radical initiator in an aqueous phase comprising an aqueous medium comprising at least one suspension stabilizer or surfactant and b) initiating polymerization of the oil phase in the aqueous phase, thereby forming an adhesive microsphere transdermal drug delivery composition.

Unless otherwise indicated, all weight percentages are based on the total weight of the transdermal drug delivery composition.

DETAILED DESCRIPTION OF THE INVENTION

The transdermal drug delivery composition of the invention can be formed by a "post-addition" method, wherein the polymerized microsphere component is blended with the softening agent and/or drug under such conditions as to cause the softening agent and/or drug to be incorporated into the microsphere. This post-addition method of preparing the transdermal drug delivery composition of the invention comprises the steps of:

(a) providing a polymeric microsphere component;
(b) blending the polymeric microsphere component with a softening agent and/or a drug and, optionally, a solvent capable of dissolving the softening agent and/or drug and/or of swelling the polymeric microsphere component; and
(c) removing the solvent.

The polymeric microsphere component of the inventive compositions can be prepared by suspension, dispersion, direct emulsion and modified emulsion techniques. Preferably, the polymeric microsphere component is prepared according to the suspension polymerization methods described in, for example, U.S. Pat. Nos. 3,691,140; 4,166,152; 4,495,318; 4,786,696; 4,988,467; 5,045,569; 5,508,313; and 5,571,617 and PCT Pat. Appls. WO 96/01280; WO 97/46633; and WO 97/46634, the disclosures of which are incorporated herein by reference. The preferred polymeric microsphere components are comprised of acrylate or vinyl ester microspheres.

In the preferred suspension polymerization methods, the acrylate or vinyl ester microspheres can typically be prepared by forming an oil phase comprising (meth)acrylic acid ester and/or vinyl ester monomers, optionally also containing free radically polymerizable polar comonomers, and an oil soluble free radical initiator in a water phase that comprises an aqueous medium having at least one suspension stabilizer or surfactant. Depending on the types and amounts of monomers, comonomers, crosslinking agents, oligomeric or polymeric additives, stabilizers, surfactants, reaction conditions, and other composition and process alternatives employed, these microspheres can be hollow (i.e., having at least one internal void or cavity) or solid (i.e., having no internal voids or cavities); water or solvent dispersible; lightly or highly crosslinked; and possess a range of diameters (from about 0.5 to about 300 microns) and polymeric morphologies.

(Meth)acrylic acid ester monomers used in the acrylate microspheres are monofunctional unsaturated (meth)acrylate esters of non-tertiary alkyl alcohols. The alkyl groups of these alcohols preferably contain from 4 to 14 (more preferably 4 to 10) carbon atoms. Examples of useful monomers include sec-butyl acrylate, n-butyl acrylate, isoamyl acrylate, 2-methylbutyl acrylate, 4-methyl-2-pentyl acrylate, 2-ethylhexyl acrylate, isooctyl acrylate, isononyl acrylate, isodecyl methacrylate, isodecyl acrylate, dodecyl acrylate, tetradecyl acrylate, and mixtures thereof. Particularly preferred are n-butyl acrylate, sec-butyl acrylate, isoamyl acrylate, 2-ethylhexyl acrylate, isooctyl acrylate, isononyl acrylate, isodecyl acrylate, and mixtures thereof. Of these, isooctyl acrylate and 2-ethylhexyl acrylate are the most preferred.

Vinyl ester monomers useful for providing the vinyl ester microspheres are unsaturated vinyl esters derived from linear or branched carboxylic acids having 1 to 14, preferably 7 to 12, carbon atoms (not counting the carboxyl carbon atom). Suitable vinyl ester monomers include vinyl propionate, vinyl pelargonate, vinyl hexanoate, vinyl caprate, vinyl 2-ethylhexanoate, vinyl octanoate, vinyl decanoate, vinyl laurate, and mixtures thereof. Particularly preferred are vinyl caprate, vinyl 2-ethylhexanoate, vinyl laurate, and mixtures thereof.

(Meth)acrylate ester or other vinyl monomers which, as homopolymers, have glass transition temperatures higher than about −20 to 0° C., e.g., ethyl acrylate, tert-butyl acrylate, isobornyl acrylate, butyl methacrylate, vinyl acetate, acrylonitrile, mixtures thereof, and the like, may be used in conjunction with one or more of the (meth)acrylate and vinyl ester monomers provided that the glass transition temperature of the resulting microspheres are below about −0° C.

Acrylate or vinyl ester microspheres useful in the present invention can further comprise a free radically polymerizable polar comonomer copolymerizable with the (meth)acrylic acid ester or vinyl ester monomer. The free radically polymerizable polar comonomers may be added to improve or modify cohesive strength, storage stability, and glass transition temperature of the microspheres. Preferably the polar monomer is present in an amount of no more than about 1 to about 20 parts by weight based on the total weight of the monomers.

In addition to their copolymerizability with the (meth)acrylic acid ester or vinyl ester monomer, the free radically polymerizable polar comonomers are monomers that are both oil and water soluble and include one of the following polar substituents: amide, nitrile, hydroxyl and carboxylic acid (including acid salt) groups. Suitable classes of polar monomers include monoolefinic monocarboxylic acids, monoolefinic dicarboxylic acids, salts thereof, acrylamides, N-substituted acrylamides, N-vinyl lactams, and mixtures of the foregoing. Representative examples of these classes of useful polar monomers include acrylic acid, methacrylic acid, itaconic acid, crotonic acid, maleic acid, fumaric acid, sulfoethyl methacrylate, N-vinyl pyrrolidone, N-vinyl caprolactam, acrylamide, t-butyl acrylamide, dimethylamino ethyl acrylamide, N-octyl acrylamide, hydroxy ethyl acrylate, and hydroxy ethyl methacrylate. Ionic monomers such as sodium methacrylate, ammonium acrylate, sodium acrylate, trimethylamine p-vinyl benzimide, N,N-dimethyl-N-(beta-methoxy-ethyl) ammonium propionate betaine, trimethylamine methacrylamide, 1,1-dimethyl- 1-(2,3-dihydroxypropyl)amine methacrylamide, and mixtures thereof are also useful. Particularly preferred polar comonomers are acrylic acid, sodium acrylate, N-vinyl pyrrolidone, and mixtures thereof.

The polymeric microspheres useful in the invention may also contain a multifunctional free-radically polymerizable crosslinking agent. Such crosslinking agents can enhance the cohesive strength and solvent insolubility of the individual microspheres by internally crosslinking them. "Multifunctional" refers to crosslinking agents that possess two or more free-radically polymerizable olefinically unsaturated groups. Useful multifunctional crosslinking agents include (meth)acrylic esters of diols (e.g., butanediol), triols (e.g., glycerol), and tetrols (e.g., pentaerythritol); polymeric multifunctional (meth)acrylates (e.g., poly(ethylene oxide) diacrylate and poly(ethylene oxide) dimethacrylate); polyvinylic compounds (e.g., substituted and unsubstituted divinylbenzene); difunctional urethane acrylates; and mixtures thereof.

When a crosslinking agent is employed, it is typically used at a level of up to about 0.15 equivalent weight percent. At levels above about 0.15 equivalent weight percent, the microspheres tend to lose their pressure sensitive adhesive qualities and eventually become non-tacky to the touch at room temperature. Non-tacky and tacky microspheres are useful in this invention. However, the level of crosslinking affects particle swellability; the higher the degree of crosslinking, the lower the particle swelling. To ensure high particle swelling and achieve the desired rheological properties, low levels of crosslinking agent are desired.

The "equivalent weight percent" of a given compound is defined as the number of equivalents of that compound divided by the total number of equivalents of free-radically polymerizable monomers in the total polymerizable composition. An equivalent is the number of grams divided by the equivalent weight. The equivalent weight is defined as the molecular weight divided by the number of polymerizable groups in the monomer. In the case of those monomers with only one polymerizable group, the equivalent weight is equal to the molecular weight.

Crosslinking of the microspheres may also be controlled with the use of chain transfer agents. Useful chain transfer agents are those which are normally suitable for free radical polymerization of acrylates. The chain transfer agents useful in the practice of the invention include, but are not limited to, carbon tetrabromide, n-dodecyl mercaptan, isooctylthiolglycolate, and mixtures thereof. If used, the chain transfer agent(s) are present in amounts of about 0.01 to about 1 percent by weight of the total polymerizable composition.

Useful oil soluble free-radical initiators are those which are normally suitable for free radical polymerization of acrylate or vinyl ester monomers and which are oil soluble and have very low solubility in water, typically less than 1 g/100 g water at 20° C. Examples of such initiators include azo compounds, hydroperoxides, peroxides, and the like, and photoinitiators such as benzophenone, benzoin ethyl ether, 2,2-dimethoxy-2-phenyl acetophenone. The initiator is generally used in an amount ranging from about 0.01 percent up to about 10 percent by weight of the total polymerizable composition, preferably up to about 5 percent.

Use of a substantially water soluble polymerization initiator, such as those generally used in emulsion polymerizations, causes formation of substantial amounts of latex. During suspension polymerization, any significant formation of latex is undesirable because of the extremely small particle size.

Surfactants will typically be present in the reaction mixture, preferably in an amount of no greater than about 10 parts by weight per 100 parts by weight of polymerizable monomer, more preferably no greater than about 5 parts by weight, and most preferably in the range of 0.5 to 3 parts by weight per 100 parts by weight of polymerizable monomer.

Useful surfactants (also known as emulsifiers) include anionic, cationic, or nonionic surfactants and include but are not limited to anionic surfactants, such as alkylarylether sulfates and sulfonates such as sodium alkylarylether sulfate, e.g., Triton™ X200, available from Rohm and Haas, alkylarylpolyether sulfates and sulfonates such as alkylarylpoly(ethylene oxide) sulfates and sulfonates, preferably those having up to about four ethyleneoxy repeat units, and alkyl sulfates and sulfonates such as sodium lauryl sulfate, ammonium lauryl sulfate, triethanolamine lauryl sulfate, and sodium hexadecyl sulfate, alkyl ether sulfates and sulfonates such as ammonium lauryl ether sulfate, and alkylpolyether sulfate and sulfonates such as alkyl poly(ethylene oxide) sulfates and sulfonates, preferably those having up to about four ethyleneoxy units. Alkyl sulfates, alkyl ether sulfates, and alkylarylether sulfates are preferred. Additional anionic surfactants can include, for example, alkylaryl sulfates and sulfonates, for example sodium dodecylbenzene sulfate and sodium dodecylbenzene sulfonate, sodium and ammonium salts of alkyl sulfates, for example sodium lauryl sulfate, and ammonium lauryl sulfate; non-ionic surfactants, such as ethoxylated oleoyl alcohol and polyoxyethylene octylphenyl ether; and cationic surfactants, such as a mixture of alkyl dimethylbenzyl ammonium chlorides wherein the alkyl chain contains from 10 to 18 carbon atoms. Amphoteric surfactants are also useful in the present invention and include for example sulfobetaines, N-alkylaminopropionic acids, and N-alkylbetaines.

Optionally, a polymeric stabilizer may be used and if used is present in an amount of about 0.05 to about 3 parts by weight per 100 parts by weight of the microspheres, preferably about 0.1 to about 1.5 parts by weight per 100 parts by weight of the microspheres. Advantageously, the presence of the stabilizer permits the use of relatively low amounts of surfactant while still obtaining microspheres.

Any polymeric stabilizer that effectively provides sufficient stabilization of the final polymerized droplets and prevents agglomeration within a suspension polymerization process is useful in the present invention.

Exemplary polymeric stabilizers include salts of polyacrylic acids of greater than 5000 weight average molecular weight (for example, ammonium, sodium, lithium and potassium salts), polyvinyl alcohol, carboxy modified polyacrylamides (for example, Cyanamer™ A-370 from American Cyanamid), copolymers of acrylic acid and dimethylaminoethylmethacrylate and the like, polymeric quaternary amines (for example, General Analine and Film's Gafquat™ 755, a quaternized polyvinyl-pyrrolidone copolymer, or Union Carbide's "JR-400", a quaternized amine substituted cellulosic), cellulosics, and carboxy-modified cellulosics (for example, Hercules' Natrosol™ CMC Type 7L, sodium carboxy methylcellulose).

The microspheres tend to be bead or pearl shaped, although they may be more spheroidal. Typically, they have a volume average diameter of about 0.5 to about 300 microns (more preferably, about 1 to about 100 microns) before swelling. The microspheres may be solid, hollow or a mixture thereof and are preferably elastomeric. As used herein, "elastomeric" means amorphous or noncrystalline materials that can be stretched and that will retract rapidly to substantially their original dimensions upon release of the force. Hollow microspheres contain one or more voids; i.e., one or more spaces completely within the walls of a polymerized microsphere. Typically, the hollow portion is less than 100 microns in average diameter.

Microsphere components comprising hollow microspheres are preferred in some applications, as both the voids within the microspheres and the crosslinked microsphere matrix can be loaded with the softening agent and/or drug. If hollow microspheres are desired, they may be obtained, for example, by the "two-step" process as described in U.S. Pat. No. 4,968,562 or the "one step" process as described in U.S. Pat. No. 5,053,436, which disclosures are incorporated herein by reference.

Solid microspheres may be prepared via suspension polymerization techniques that use ionic or nonionic emulsifiers in an amount that is sufficient to generate the necessary particle and which is generally near the critical micelle concentration.

Each suspension polymerization method (whether producing hollow or solid microspheres) may be modified by withholding the addition of all or some of the free-radically polymerizable polar comonomer or other reactive components until after polymerization of the oil phase (meth)acrylic acid ester or vinyl ester monomer has been initiated. In this instance, however, these components must be added to the polymerizing mixture before 100% conversion of the (meth)acrylic acid ester or vinyl ester monomer. Similarly, a multifunctional free-radically polymerizable crosslinking agent (if used) can be added at any time before 100% conversion to polymer of the monomers of the microsphere composition. Preferably, the crosslinking agent is added before initiation occurs.

Following polymerization, a stable aqueous suspension of microspheres at room temperature is obtained. The suspension may have non-volatile solids contents of from about 10 to about 60 percent by weight. Upon prolonged standing, the suspension typically separates into two phases, one phase being aqueous and essentially free of polymer and the other phase being an aqueous suspension of the polymeric microspheres, that is, the microsphere-rich phase. Separation of the microsphere-rich phase provides an aqueous suspension having a non-volatile solids content. Alternatively, the microspheres may be isolated in an organic solvent to form a solvent dispersion if desired prior to blending with the softening agent and/or drug.

Once prepared, the microsphere component, either neat, as an aqueous suspension or as a solvent dispersion, is blended with the softening agent and/or drug.

As used herein, the term "therapeutically effective amount" means an amount effective to allow the composition to deliver sufficient drug to a subject to achieve a desired therapeutic result in the treatment of a condition. This amount will vary according to the type of drug used, the condition to be treated, the amount of time the composition is allowed to remain in contact with the skin of the subject, and other factors known to those of skill in the art. However, the amount of drug present in the transdermal drug delivery composition of the invention will generally be about 0.01 to 40 wt-%, preferably about 0.5 to 10 wt-%, based on the total weight of the composition.

Any drug that is suitable for transdermal delivery may be used in the transdermal drug delivery composition of the invention. Examples of useful drugs include, but are not limited to, antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotozoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., zileuton), and angiotensin converting enzyme inhibitors (e.g., captopril, lisinopril); other antihypertensives (e.g., propranolol); leukotriene antagonists; anti-ulceratives such as H2 antagonists; steroidal hormones (e.g., progesterone, testosterone, estradiol); antivirals and/or immunomodulators (e.g., 1-isobutyl- 1 H-imidazo[4,5-c]quinolin-4-amine, 1-(2-hydroxy-2-methylpropyl)- 1 H-imidazo [4,5-c]quinoline-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); sex hormones (e.g., estrogens, testosterone, progestins such as levonorgestrel, norethindrone, gestodene); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; antiobesity agents; and the like, as well as pharmaceutically acceptable salts and esters thereof Preferred drugs include testosterone, levonorgestrel, estradiol, and gestodene.

Suitable softening agents (softeners) include certain pharmaceutically acceptable materials that have been used as skin penetration enhancers or solubilizers in transdermal drug delivery systems. Exemplary materials include $C_8$–$C_{36}$ fatty acids such as isostearic acid, octanoic acid, and oleic acid; $C_8$–$C_{36}$ fatty alcohols such as oleyl alcohol and lauryl alcohol; lower alkyl esters of $C_8$–$C_{36}$ fatty acids such as ethyl oleate, isopropyl myristate, butyl stearate, and methyl laurate; di(lower) alkyl esters of $C_6$–$C_8$ diacids such as diisopropyl adipate; monoglycerides of $C_8$–$C_{36}$ fatty acids such as glyceryl monolaurate; tetrahydrofurfuryl alcohol polyethylene glycol ether; $C_6$–$C_{36}$ alkyl pyrrolidone carboxylates; polyethylene glycol; propylene glycol; 2-(2-ethoxyethoxy)ethanol; diethylene glycol monomethyl ether; N,N-dimethyldodecylamine-N-oxide and combinations of the foregoing. Alkylaryl ethers of polyethylene oxide, polyethylene oxide monomethyl ethers, and polyethylene oxide dimethyl ethers are also suitable, as are solubilizers such as glycerol and N-methyl pyrrolidone. The terpenes are another useful class of softeners, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Of the terpenes, terpineol, particularly α-terpineol, is preferred.

Certain drug substances function as softeners, making it unnecessary to have separate drug and softener components. Such softening drugs include nicotine, nitroglycerine, chlorpheniramine, nicotinic acid benzyl ester, orphenadrine, scopolamine, and valproic acid. If the softening drug is the only softening agent present, then it is present in an amount of at least 10 wt-% based on the total weight of the transdermal drug delivery composition. If other softening agents are present in addition to the softening drug, then the total amount of softener is at least 10 wt-%. It is understood that any desired combination of softening agents and/or softening drugs may be used.

Preferred softeners include glyceryl monolaurate, terpineol, lauryl alcohol, diisopropyl adipate, propylene glycol, isopropyl myristate, ethyl oleate, methyl laurate, 2-(2-ethoxyethoxy)ethanol, and oleyl alcohol.

While many of the softeners enumerated above are known to affect skin penetration rate, certain softeners affect aspects of performance other than and in addition to skin penetration rate. For example, they are useful in softening or increasing the compliance value and/or lowering the glass transition temperature of otherwise non-compliant (and therefore non-pressure sensitive adhesive) polymers, rendering them suitable for use as pressure sensitive skin adhesives. While such softeners have been known to adversely affect the performance of a transdermal matrix, e.g., by softening it to the point of cohesive failure (where substantial polymer residue is left on the skin after removal of a device containing the polymer from the skin) or by separating from the continuous phase of the composition, use of microspheres according to the invention allows for the inclusion of relatively large amounts of softener without giving rise to these adverse effects.

The properties desirable in a transdermal drug delivery composition are well known to those skilled in the art. For example, it is necessary that the composition remain in intimate contact with the skin in order to deliver drug at a stable rate. It is desirable for a composition to have sufficiently little cold flow that it is stable to flow upon storage, and it is also preferred that it adhere to the skin and release cleanly from the skin. In order to achieve skin contact, clean release, preferred levels of adhesion, and resistance to cold flow the amount and structure of the monomers in the polymeric microspheres, and the amount and structure of the softener are selected such that the composition has a compliance value (measured according to the test method set forth in detail below) in the range of about $3 \times 10^{-6}$ cm$^2$/dyne to about $1 \times 10^{-3}$ cm$^2$/dyne, preferably in the range of about $1 \times 10^{-5}$ cm$^2$/dyne to about $5 \times 10^{-4}$ cm$^2$/dyne, more preferably about $1 \times 10^{-5}$cm$^2$/dyne to about $5 \times 10^{-5}$ cm$^2$/dyne. Compliance values outside the broad range recited above sometimes are obtained from compositions that are suitable for use as pressure sensitive adhesive transdermal drug delivery compositions. However, those compositions having substantially lower compliance values will generally be relatively stiff and have less than optimal skin contact and adhesion to skin. Those compositions having substantially higher compliance values will generally have less than optimal cold flow and might leave substantial residue when removed from the skin.

The softener is present in amount of at least 10 wt-%, based on the total weight of the transdermal drug delivery composition, in order to provide enhanced delivery of the drug and maintain acceptable adhesive properties. Preferably the softener is present in an amount of about 15 to about 50 wt-%, and more preferably about 25 to about 50 wt-%.

The softener and optional drug are typically combined with a solvent and incorporated into the microsphere component of the composition in the manner described above. However, suitable compositions could also be prepared by separately incorporating the drug and the softener into the microspheres, and then combining the drug/microsphere and softener/microsphere mixtures to obtain the final composition. Alternatively, softener containing microspheres could be blended with a drug and a conventional (i.e., non-microsphere) adhesive to obtain the final composition.

In another aspect of the invention, the transdermal drug delivery composition can be prepared by a modification of the previously described suspension polymerization procedures through the addition of all or any portion of the softening agent and/or drug to the free radically polymerizable suspension mixture. To be useful in this method, the softening agent and drug, if one is used, should be sufficiently oil-soluble to be miscible in the oil phase of the suspension polymerization mixture and also be non-reactive under free radical polymerization and other reactive conditions. By "non-reactive" it is meant that the softening agent or drug contains no ethylenic unsaturation or other functionalities that could coreact or otherwise interfere with the polymerization of the free radically reactive suspension mixture and/or that the efficacy of the softening agent or drug agent is not significantly degraded under reaction conditions.

The in situ method of preparing the transdermal drug delivery composition of the present invention comprises the steps of:

(a) forming an oil phase comprising (meth)acrylic acid ester and/or vinyl ester monomers and a non-reactive, oil soluble softening agent and/or drug and an oil soluble free radical initiator in an aqueous phase that comprises an aqueous medium having at least one suspension stabilizer or surfactant;

(b) initiating polymerization of the oil phase in the aqueous phase;

(c) optionally, adding additional non-reactive, oil soluble softening agent and/or drug to the in situ polymerized adhesive microsphere transdermal drug delivery composition.

Backings used as substrates for transdermal drug delivery devices coated with the transdermal drug delivery composition of the present invention may be materials that are conventionally used as a tape backing or may be of other flexible material that is substantially inert to the ingredients of the transdermal drug delivery composition. Such backings include, but are not limited to, those made from materials selected from the group consisting of poly (propylene), poly(ethylene), poly(vinyl chloride), polyester (e.g., poly(ethylene terephthalate), such as those available under the trade designation of "Scotch" film 8050 from 3M)), polyamide films such as that available from DuPont Co., Wilmington, Del., under the trade designation "KAPTON," cellulose acetate, and ethyl cellulose. Backings may also be of woven fabric formed from threads of synthetic or natural materials such as cotton, nylon, rayon, glass, or ceramic material, or they may be of nonwoven fabric such as air laid webs of natural or synthetic fibers or blends of these. In addition, the backing may be formed of materials selected from the group consisting of metal, metallized polymeric film, and ceramic sheet material.

Preferred materials include, but are not limited to, plastics such as polyethylene, polypropylene, polyesters, cellulose acetate, poly(vinyl chloride), and poly(vinylidine fluoride), as well as paper or other substrates coated or laminated with such plastics. These coated papers or thermoplastic films are often siliconized or otherwise treated to impart improved release characteristics. One or both sides of the backings or liners could have such release characteristics.

The devices of the invention can have a variety of configurations. The composition can be present as a single layer wherein the composition is made up of microspheres containing both softener and/or drug; a mixture of softener containing microspheres and drug containing microspheres; or softener containing microspheres blended with a drug and conventional adhesive. It is also possible to use compositions according to the invention in multiple layers. For example, a layer of softener containing microspheres could be laminated to a layer of drug in a conventional adhesive or to a layer of drug containing microspheres. Such layers can be of a uniform thickness or they can be arranged in one or more gradients. Other layers can be present, such as scrims, membranes and the like. All references to softener containing microspheres also include microspheres containing softener and drug.

Typical coating methods that can be used to prepare adhesive articles according to the present invention, include both solvent coating and water-based coatings and techniques commonly known to those skilled in the art.

Objects and advantages of this invention are further illustrated by the following examples. The particular materials and amounts thereof recited in these examples as well as other conditions and details, should not be construed to unduly limit this invention. All materials are commercially available except where stated or otherwise made apparent. All parts and percentages used herein are by weight, unless otherwise specified.

Compliance Test Method

The compliance values given in the examples below were obtained using a modified version of the Creep Compliance Procedure described in U.S. Pat. No. 4,737,559 (Kellen). The release liner is removed from a sample of the material to be tested. The exposed surface is folded back on itself in the lengthwise direction to produce a "sandwich" configuration, i.e., backing/adhesive/backing. The "sandwiched" sample is passed through a laminator then two test samples of equal area are cut using a rectangular die. One test sample is centered on the stationary plate of a shear-creep rheometer with the long axis of the test sample centered on the short axis of the plate. The small, non-stationary plate of the shear-creep rheometer is centered over the first sample on the stationary plate such that the hook is facing up and toward the front of the rheometer. The second test sample is centered on the upper surface of the small, non-stationary plate matching the axial orientation of the first test sample. The large non-stationary plate is placed over the second test sample and the entire assembly is clamped into place. The end of the small, non-stationary plate that is opposite the end with the hook is connected to a chart recorder. A string is connected to the hook of the small, non-stationary plate and extended over the front pulley of the rheometer. A weight (e.g. 500 g) is attached to the free end of the string. The chart recorder is started and at the same time the weight is quickly released so that it hangs free. The weight is removed after exactly 3 minutes have elapsed. The displacement is read from the chart recorder. The compliance is then calculated using the equation:

$$J = 2\frac{AX}{hf}$$

where A is the area of one face of the test sample, h is the thickness of the adhesive mass (i.e., two times the thickness of the adhesive layer on the tested sample), X is the displacement and is the force due to the mass attached to the string. Where A is expressed in cm$^2$, h in cm, X in cm and f in dynes, the compliance value is given in cm$^2$/dyne.

In Vitro Skin Penetration Test Method

The skin penetration data given in the examples below was obtained using the following test method. A diffusion cell is used with hairless mouse skin.

When a transdermal delivery device is evaluated, the release liner is removed from a 2.0 cm$^2$ patch and the patch is applied to the skin and pressed to cause uniform contact with the skin. The resulting patch/skin laminate is placed patch side up across the orifice of the lower portion of the diffusion cell. The diffusion cell is assembled and the lower portion is filled with 10 mL of warm (32° C.) receptor fluid so that the receptor fluid is in contact with the skin. The receptor fluid is stirred using a magnetic stirrer. The sampling port is covered except when in use.

The cell is then placed in a constant temperature (32±2° C.) and humidity (50±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals and immediately replaced with fresh fluid. The withdrawn fluid is filtered through a 0.45 μM filter then analyzed for drug content using high performance liquid chromatography. The cumulative amount of drug penetrating the skin and the flux rate are calculated.

Drug Release Test Method

The drug release data given in the examples below was obtained using the following test method.

The drug loaded microspheres are coated on a 2 mil (51 μM) polyester backing then oven dried at 185° F. (85° C.) for 20 minutes and at 210° F. (99° C.) for 20 minutes. A patch (5 cm$^2$) is cut from the dried web. The patch is fastened to a steel plate using double sided adhesive tape such that the drug microsphere adhesive layer is exposed to the release medium. The steel plate is immersed in a 30% ethyl alcohol aqueous release medium. The medium is maintained at 32° C. and stirred by means of a magnetic stirrer at moderate speed (75 rpm) throughout the experiment. At specified time points a 2 mL portion of the release medium is removed and immediately replaced with 2 mL of fresh medium. The withdrawn medium is filtered through a 0.22 μM filter to remove any particulate then assayed for drug content using high performance liquid chromatography. The cumulative amount of drug released is calculated.

Tack Test Method

The tack values reported in the examples below were obtained using a to Digital Polyken Probe Tack Tester, Model 80-02-01 (Testing Machines, Inc., Amityville, N.Y.). The machine settings were as follows: speed: 0.5 cm/second, dwell: 2 seconds; mode: peak. A stainless steel probe was used. The result of the test is the force required to break the bond between the probe and the surface of the test sample. The force is measured in "grams of tack".

EXAMPLE 1

A one-liter baffled reaction flask equipped with mechanical stirrer, condenser, and inlet-outlet lines for vacuum and argon was charged with 450 gs of deionized water and 6.0 g of ammonium lauryl sulfate (Standpol™ A, available from Henkel AG). The reactor was degassed then refilled with argon. The agitation was set at 400 rpm and the reactor was heated to 68° C. A mixture containing 141 g of isooctyl acrylate, 9 g of acrylic acid and 0.71 g of benzoyl peroxide ( Lucidol-70, available from Elf Atochem) was prepared in a jar. After the initiator dissolved, the mixture was charged to the reactor at 68° C. The temperature of the reactor was then reset to 65° C. for 22 hours. An argon purge was maintained during the polymerization. After 22 hours, the suspension was cooled to ambient temperature. The reactor was then emptied, the suspension was coagulated with cetyl trimethyl ammonium chloride and then collected. The resulting microspheres (94:6 isooctyl acrylate:acrylic acid) had a hollow morphology and particle size of 45.5 μm. The microspheres were washed with isopropanol and redispersed in isopropanol before use.

These microspheres were used to prepare an adhesive microsphere delivery system containing levonorgestrel and isopropyl myristate as follows. A solution of levonorgestrel in methanol was prepared by dissolving 0.0252 g of levonorgestrel in 1.0 g of methanol. Isopropyl myristate (0.5549 g), 5.0 g of microspheres (14.75 g of a dispersion in isopropanol at 33.9% solids) and 35.0 g of ethyl acetate were combined and mixed on a shaker table for a minimum of 16 hours. A 25.15 g portion of the resulting mixture was combined with the levonorgestrel solution and mixed on a shaker table for a minimum of 16 hours. The resulting formulation was knife coated with a 27 mil (686 μM) die gap onto a silicone release liner, oven dried at 110° F. (43° C.) for 20 minutes. The resulting adhesive coating contained 1 percent levonorgestrel, 10 percent isopropyl myristate and 89 percent adhesive. The coating was uniform and microscopic examination showed that it was substantially free of drug crystals. The coated liner was laminated to a polyester backing.

EXAMPLES 2–5

Using the general method of Example 1 and the same microsphere adhesive, a series of delivery systems was prepared in which the amount of isopropyl myristate varied. In all instances the adhesive coating contained 1 percent by weight levonorgestrel and the adhesive was 94:6 IOA:AA hollow microspheres. The weight percent of isopropyl myristate is shown in Tables 1 and 2 below.

The tack and compliance were determined for the delivery systems of Example 1–5 using the test methods described above. The results are shown in Table 1 below where each tack value is the average of 5 independent determinations and each compliance value is the average of 3 independent determinations.

TABLE 1

| Example Number | Isopropyl Myristate (weight percent) | Tack (g) | Compliance (cm²/dynes) |
| --- | --- | --- | --- |
| 1 | 10 | 294 | $0.92 \times 10^{-5}$ |
| 2 | 20 | 235 | $1.23 \times 10^{-5}$ |
| 3 | 30 | 227 | $3.42 \times 10^{-5}$ |
| 4 | 40 | 141 | $3.97 \times 10^{-5}$ |
| 5 | 50 | 112 | $6.36 \times 10^{-5}$ |

Penetration of levonorgestrel through hairless mouse skin from the delivery system of Examples 1–5 was determined using the test method described above. The receptor solution was 30% by weight m-pyrol in water. Samples were refrigerated prior to content analysis with storage times of no more than two days. The results are shown in Table 2 below where each flux value is the average of 3 independent determinations. The 0–24 hours value is the average over the entire 24 hour time period.

TABLE 2

| Example Number | Isopropyl Myrsistate Weight percent | Flux ($\mu$g levonorgestrel/cm²/hr) 0–8 hr | 8–24 hr | 0–24 hr |
| --- | --- | --- | --- | --- |
| 1 | 10 | 0.27 | 0.30 | 0.29 |
| 2 | 20 | 0.32 | 0.37 | 0.36 |
| 3 | 30 | 0.22 | 0.32 | 0.28 |
| 4 | 40 | 0.31 | 0.40 | 0.37 |
| 5 | 50 | 0.42 | 0.43 | 0.43 |

EXAMPLE 6

A one-liter baffled reaction flask equipped with mechanical stirrer, condenser, and inlet-outlet lines for vacuum and argon was charged with 450 g of deionized water and 6.0 g of ammonium lauryl sulfate (Standpol™ A). The reactor was degassed then refilled with argon. The agitation was set at 400 rpm and the reactor was heated to 68° C. A mixture containing 141 g of isooctyl acrylate, 9 g of acrylic acid and 0.71 g of benzoyl peroxide( Lucidol-70) was prepared in a jar. After the initiator dissolved, the mixture was charged to the reactor at 68° C. The temperature of the reactor was then reset to 65° C. for 22 hours. An argon purge was maintained during the polymerization. After 22 hours, the suspension was cooled to ambient temperature. The reactor was then emptied, the suspension was coagulated with cetyl trimethyl ammonium chloride then collected. The resulting microspheres (94:6 isooctyl acrylate:acrylic acid) had a multiple void hollow morphology and particle size of 64.4 $\mu$m. The microspheres were washed with isopropanol and redispersed in isopropanol before use.

These microspheres were used to prepare an adhesive microsphere delivery system containing testosterone as follows. A blend of 4% w/w testosterone in microsphere adhesive was prepared by combining 0.977 g of testosterone with 23.445 g of microspheres (85.63 g of a dispersion in isopropanol at 27.38 % solids) then mixing on a shaker table for a minimum of 16 hours. A portion (7.38 g) of the blend was combined with 15.0 g of ethyl acetate. The resulting formulation was knife coated with a 27 mil (686 $\mu$M) die gap onto a silicone release liner, oven dried at 110° F. (43° C.) for 20 minutes. The resulting adhesive coating contained 4 percent testosterone and 96 percent adhesive. The coating was uniform and microscopic examination showed that it was substantially free of drug crystals. The coated liner was laminated to a polyester backing.

EXAMPLE 7

An adhesive microsphere delivery system containing testosterone and terpineol was prepared as follows. A 15.2 percent w/w stock solution of testosterone in terpineol was prepared by dissolving 8.0261 g of testosterone in 44.9667 g of terpineol. A portion (0.598 g) of this solution was combined with 7.497 g of the 4 percent w/w testosterone microsphere adhesive blend prepared in Example 6 and 21.6 g of ethyl acetate and then mixed on a shaker table for a minimum of 16 hours. The resulting formulation was knife coated with a 27 mil (686 $\mu$M) die gap onto a silicone release liner then oven dried at 110° F. (43° C.) for 20 minutes. The resulting adhesive coating contained 6.45 weight percent testosterone, 20 weight percent terpineol and 73.55 weight percent adhesive. The coating was uniform and microscopic examination showed that it was substantially free of drug crystals. The coated liner was laminated to a polyester backing.

EXAMPLES 8–10

Using the general method of Example 7 a series of delivery systems in which the amount of testosterone and the amount of terpineol were varied was prepared. In all instances the microsphere adhesive prepared in Example 6 was used. The weight percent of testosterone and of terpineol are shown in Table 3 below.

Penetration of testosterone through hairless mouse skin from the delivery systems of Examples 6–10 was determined using the test method described above. The receptor solution was 30% by weight m-pyrol in water. Samples were refrigerated prior to content analysis with storage times of no more than two days. The results are shown in Table 3 below where each flux value is the average of 3 independent determinations. The 0–24 hours value is the average over the entire 24 hour time period.

TABLE 3

| Example Number | Testosterone (wt percent) | Terpineol (wt percent) | Flux ($\mu$g testosterone/cm²/hr) 0–4 hr | 4–8 hr | 8–24 hr | 0–24 hr |
| --- | --- | --- | --- | --- | --- | --- |
| 6 | 4 | 0 | 0.8 | 2.0 | 2.1 | 1.9 |
| 7 | 6.45 | 29 | 2.0 | 4.2 | 3.5 | 3.3 |
| 8 | 7.68 | 30 | 1.5 | 2.2 | 1.9 | 1.9 |
| 9 | 8.76 | 40 | 1.6 | 2.8 | 2.6 | 2.4 |
| 10 | 9.93 | 50 | 2.4 | 9.1 | 5.8 | 5.8 |

EXAMPLE 11

An adhesive microsphere delivery system containing terpineol was prepared as follows. Terpineol (2.50 g), 10.0 g of 94:6 IOA:AA microspheres (36.52 g of a dispersion in isopropanol at 27.38 % solids, Example 6) and 26.52 g of ethyl acetate were combined then mixed on a shaker table for a minimum of 16 hours. The resulting formulation was knife coated with a 20 mil (508 $\mu$M) die gap onto a silicone release liner then oven dried at 110° F. (43° C.) for 20 minutes. The resulting adhesive coating contained 20 percent terpineol and 80 percent adhesive. The coating was uniform. The coated liner was laminated to a polyester backing.

EXAMPLES 12–14

Using the general method of Example 11 a series of delivery systems in which the amount of terpineol was varied was prepared. In all instances the ahesive microspheres prepared in Example 6 were used. The weight percent of terpineol is shown in Table 4 below.

The tack and compliance were determined for the delivery systems of Example 11–14 using the test methods described above. The results are shown in Table 4 below where each tack value is the average of 5 independent determinations and each compliance value is the average of 3 independent determinations.

TABLE 4

| Example Number | Terpineol (weight percent) | Tack (g) | Compliance (cm²/dynes) |
|---|---|---|---|
| 11 | 20 | 399 | $0.82 \times 10^{-5}$ |
| 12 | 30 | 354 | $1.94 \times 10^{-5}$ |
| 13 | 40 | 274 | $3.44 \times 10^{-5}$ |
| 14 | 50 | 171 | $5.56 \times 10^{-5}$ |

EXAMPLE 15

A one-liter baffled reaction flask equipped with mechanical stirrer, condenser, and d inlet-outlet lines for vacuum and argon was charged with 390 g of deionized water and 8.4 grams of ammonium lauryl sulfate (Standpol™ A). The reactor was degassed then refilled with argon. The agitation was set at 425 rpm and the reactor was heated to 68° C. A mixture containing 210 g of isooctyl acrylated and 0.69 g of 2,2'-azobis(2-methylbutanenitrile) was prepared in a jar. After the initiator dissolved, the mixture was charged to the reactor at 68° C. The temperature of the reactor was then reset to 60° C. for 22 hours. An argon purge was maintained during the polymerization. After 22 hours, the suspension was cooled to ambient temperature. The reactor was then emptied, the suspension was coagulate with isopropanol and collected. The resulting microspheres had a hollow morphology and particle size of up to 50 $\mu$m. The microspheres were redispersed 11/89 isopropanol/ethyl acetate before use.

the microspheres were used to prepare an adhesive microsphere delivery system containing testosterone as follows. A blend of 4% w/w testosterone in microsphere adhesive was prepared by combining 0.8358 g of testosterone with 20.0 g of the microspheres (181.88 g of a dispersion in isopropanol/ethyl acetate 11/89 w/w at 11% solids) then mixing on a shaker table for a minimum of 16 hours. A portion of the resulting formulation was knife coated with a 26 mil (660 $\mu$M) die gap onto a fluoropolymer release liner, oven dried at 110° F. (43° C.) for 20 minutes. The resulting adhesive coating contained 4 percent testosterone and 96 present adhesive. The coating was uniform and microscopic examination showed that it was initially free of drug crystals. The coated liner was laminated to a polyester backing. Samples were stored in sealed, foil-lined polyester pouches. After one week of storage, microscopic examination showed that numerous crystals had formed.

EXAMPLE 16

An adhesive microsphere delivery system containing testosterone and terpineol was prepared as follows. A 14.0 percent w/w stock solution of testosterone in terpineol was prepared by combining 7.347 g of testosterone with 41.64 g of terpineol, mixing on a shaker table for 3 days then filtering to remove undissolved testosterone. Solutions prepared by this method have been assayed by high performance liquid chromatography as 1:100 dilution in methanol and shown to contain 14.0 weight percent testosterone. A portion (0.35 g) of this solution was combined with a portion (29.05 g) of the formulation prepared in Example 15 then mixed on a platform shaker for a minimum of 16 hours. The resulting formulation was knife coated with a 26 mil (660 $\mu$M) die gap onto a fluoropolymer coated release liner then oven dried at 110° F (43° C.) for 20 minutes. The resulting adhesive coating contained 4.8 weight percent testosterone, 8.2 weight percent terpineol and 87.0 weight percent adhesive. The coating was uniform and microscopic examination showed that it was initially free of drug crystals. The coated liner was laminated to a polyester backing. Samples were stored in sealed, foil-lined polyester pouches. After one week of storage, microscopic examination showed that numerous crystals had formed.

EXAMPLE 17–19

Using the general method of Example 16 a series of delivery systems in which the amount of testosterone and the amount of terpineol were varied was prepared. In all instances the adhesive was IOA hollow microspheres. The weight percent of testosterone and of terpineol are shown in Table 5 below. In all three examples the coating was uniform and microscopic examination showed that it was initially free of drug crystals; but, after one week of storage, microscopic examination showed that numerous crystals had formed in all three examples.

EXAMPLE 20

Using the general method of Example 16 a delivery system containing 8.8 percent testosterone, 42.3 percent terpineol and 48.9 percent IOA microsphere adhesive was prepared. The coating was uniform and microscopic examination showed that the coating was substantially free of drug crystals both initially and after storage for 5 weeks.

Penetration of testosterone through hairless mouse skin from the delivery systems of Examples 16–20 was determined using the test method described above. The penetration test was run on initial samples. The receptor solution was 30% by weight m-pyrol in water. Samples were refrigerated prior to content analysis with storage times of no more than two days. The results are shown in Table 3 below where each flux value is the average of 3 independent determinations. The 0–24 hours value is the average over the entire 24 hour time period.

TABLE 5

| Example Number | Testosterone (wt percent) | Terpineol (wt percent) | Flux ($\mu g$ testosterone/cm$^2$/hr) | | | |
|---|---|---|---|---|---|---|
| | | | 0–4 hr | 4–8 hr | 8–24 hr | 24–28 hr |
| 15 | 4 | 0 | 1.9 | 3.1 | 2.1 | 1.7 |
| 16 | 4.8 | 8.2 | 2.9 | 4.1 | 3.6 | 3.5 |
| 17 | 5.8 | 16.6 | 3.8 | 4.9 | 3.9 | 3.8 |
| 18 | 6.8 | 25.1 | 2.9 | 6.2 | 4.3 | 3.5 |
| 19 | 7.8 | 33.8 | 3.3 | 7.4 | 5.6 | 4.0 |
| 20 | 8.8 | 42.3 | 9.3 | 31.4 | 18.5 | 10.4 |

EXAMPLE 21

A half-liter baffled reaction flask equipped with mechanical stirrer, condenser, and inlet-outlet lines for vacuum and argon was charged with 112.5 g of deionized water and 1.5 g of ammonium lauryl sulfate (Standpol™ A). The reactor was degassed then refilled with argon. The agitation was set at 300 rpm and the reactor was heated to 68° C. Isooctyl acrylate (36.75 g) and 0.75 g of β-estradiol-3-benzoate were combined in a jar then heated (about 50 ° C.) until the drug was completely dissolved in the monomer. Benzoyl peroxide (0.18 g of Lucidol-70) was added to the jar. After the initiator dissolved, the mixture was charged to the reactor at 68° C. The temperature of the reactor was then reset to 65° C. for 22 hours. An argon purge was maintained during the polymerization. After 22 hours, the suspension was cooled to ambient temperature. The microspheres were stable in the aqueous phase. The reactor was then emptied and the suspension was filtered through cheese cloth to remove agglomerates. Under optical microscopy the resulting microspheres were found to be a mixture of several morphologies: hollow, solid, multiple discrete void and multiple chain void. Particle size was determined using Particle Image Analysis and found to be 24.90 $\mu m$. A sample was coated on a 2 mil (51 $\mu M$) polyester backing then oven dried at 185° F. (85° C.) for 20 minutes and at 210° F. (99° C.) for 20 minutes. The compliance was measured using the test method described above and found to be $0.1 \times 10^{-5}$ cm$^2$/dyne.

EXAMPLE 22

A half-liter baffled reaction flask equipped with mechanical stirrer, condenser, and inlet-outlet lines for vacuum and argon was charged with 112.5 g of deionized water and 1.5 g of ammonium lauryl sulfate (Standpol™ A). The reactor was degassed then refilled with argon. The agitation was set at 300 rpm and the reactor was heated to 68° C. Isooctyl acrylate (34.9 g), 1.85 g of N-vinyl pyrrolidone, 0.094 g of 1,6-hexanediol diacrylate and 0.75 g of β-estradiol-3-benzoate were combined in a jar then heated (about 50° C.) until the drug was completely dissolved in the monomer mixture. Benzoyl peroxide (0.36 g of Lucidol-70) was added to the jar. After the initiator dissolved, the mixture was charged to the reactor at 68° C. The temperature of the reactor was then reset to 65° C. for 22 hours. An argon purge was maintained during the polymerization. After 22 hours, the suspension was cooled to ambient temperature. The microspheres were stable in the aqueous phase. The reactor was then emptied and the suspension was filtered through cheese cloth to remove agglomerates. Under optical microscopy the resulting microspheres were found to be a mixture of hollow and solid microspheres. Particle size was determined using Particle Image Analysis and found to be 29.1 $\mu M$. A sample was coated on a 2 mil (51 $\mu M$) polyester backing then oven dried at 185° F. (85° C.) for 20 minutes and at 210° F. (99° C.) for 20 minutes. The compliance was measured using the test method described above and found to be $>6.0 \times 10^{-5}$ cm$^2$/dyne.

EXAMPLE 23

An aqueous phase was prepared by neutralizing a mixture of 0.75 g acrylic acid in 56.25 g of deionized water to approximately pH 7 with ammonium hydroxide. A 40 g portion of the aqueous phase and 0.25 g of ammonium lauryl sulfate (Standpol™ A) were added to a one liter baffled reaction flask equipped with mechanical stirrer, condenser, and inlet-outlet lines for vacuum and argon. The mixture was stirred at 350 rpm while being purged with argon and heated to 68° C. An oil phase was prepared by dissolving 0.12 g of benzozyl peroxide (Lucidol 70) and 0.56 g of β-estradiol-3-benzoate in 18 g of isooctyl acrylate. The remaining portion of the aqueous phase was combined with 0.38 g sorbitan monooleate, HLB =4.3 (Arlacel 80 from ICI Specialties); the resulting mixture was homogenized to produce a foam. The oil phase was added with mixing to the foam to form an oil-in-water emulsion. The emulsion was then charged to the reactor to form a water-in-oil-in-water emulsion for polymerization. The reactor was degassed and the temperature maintained at 65° C. for 22 hours. An argon purge was maintained during the polymerization. After 22 hours the reactor was allowed to cool to ambient temperature. The microspheres were stable in the aqueous phase. The reactor was then emptied and the suspension was filtered through cheese cloth to remove agglomerates. Under optical microscopy the resulting microspheres were found to have a multiple void morphology. Particle size was determined using Particle Image Analysis and found to be 55 $\mu M$. A sample was coated on a 2 mil (51 $\mu M$) polyester backing then oven dried at 185° F. (85° C.) for 20 minutes and at 210° F. (99° C.) for 20 minutes. The compliance was measured using the test method described above and found to be $0.3 \times 10^{-5}$ cm$^2$/dyne.

EXAMPLE 24

The procedure of Example 23 was repeated using β-estradiol diacetate of β-estradiol-3-benzoate. The microspheres were found to have a multiple void morphology and a particle size of 70 $\mu M$. The compliance was found to be $>6.0 \times 10^{-5}$ cm$^2$/dyne.

The ability of the compositions of Examples 21–24 to release drug was measured using the test method described above. The values are given in Table 6 below where each value is the average of three independent determinations and the number in parenthesis is the standard error of the mean.

TABLE 6

| Example | Cumulative Amount of estradiol Released (µg) | | | |
|---|---|---|---|---|
| Number | 0 minutes | 10 minutes | 45 minutes | 180 minutes |
| 21 | 0 | 28.1 (0.4) | 50.3 (9.1) | 145.8 (13.3) |
| 22 | 0 | 5.1 (0.1) | 24.2 (1.2) | 46.9 (1.5) |
| 23 | 0 | 20.7 (1.1) | 82.0 (8.7) | 236.3 (17.4) |
| 24 | 0 | 46.7 (13.7) | 314.2 (58.1) | 581.7 (36.3) |

EXAMPLE 25

A one-liter baffled reaction flask equipped with mechanical stirrer, condenser, and inlet-outlet lines for vacuum and argon was charged with 180 g of reactor water and 4.8 g of ammonium lauryl sulfate (Standpol™ A). The degassed then refilled with argon. The agitation was set at 550 rpm and the reactor was heated to 68° C. Isooctyl acrylate (117.6 g), 2.4 g of poly(ethylene oxide)acrylate ester (AM-90G, available from Shin-Nakamura), 24 g of isopropyl myristate, 0.03 g of 1,6-hexanediol diacrylate and 0.57 g of benzoyl peroxide (Lucidol-70) were combined in a jar. After the initiator dissolved, the mixture was charged to the reactor at 68° C. The temperature of the reactor was then reset to 65° C. for 22 hours. An argon purge was maintained during the polymerization. After 22 hours, the suspension was cooled to ambient temperature. The reactor was then emptied and the suspension was filtered through cheese cloth to remove agglomerates. The resulting microspheres were found to have a fine multiple void morphology and a volume size average of 28.4 µM. A sample was thickened with acrylic latex (1 pph of UCA® polyphobe-104 from Union Carbide), coated on a chemically treated polyester liner then oven dried to provide a dried coating with a thickness of 4.4 mil (112 µM). The compliance was found to be $7.87 \times 10^{-5}$ cm$^2$/dyne.

EXAMPLE 26

The procedure of Example 25 was repeated except that the agitation was set at 450 rpm. The resulting microspheres were found to have a fine multiple void morphology and a volume size average of 45.4 µM. A sample was thickened with acrylic latex (1 pph of UCAR® polyphobe-104 from Union Carbide), coated on a chemically treated polyester liner then oven dried to provide a dried coating with a thickness of 3.8 mil (96.5 µM). The compliance was found to be $1.21 \times 10^{-5}$ cm$^2$/dyne.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A transdermal drug delivery composition comprising pressure sensitive adhesive polymeric microspheres comprising (a) at least 10 wt-% of a softening agent incorporated within the microspheres and optionally (b) a therapeutically effective amount of a drug, and wherein the softening agent-containing microspheres are inherently tacky.

2. The composition of claim 1 wherein the microspheres are hollow.

3. The composition of claim 1 wherein the microspheres are solid.

4. The composition of claim 1 wherein the microspheres are comprised of an acrylate polymer.

5. The composition of claim 4 wherein the acrylate polymer comprises a copolymer of at least one acrylic or methacrylic acid ester and at least one free radically polymerizable comonomer.

6. The composition of claim 5 wherein the at least one acrylic or methacrylic acid ester comprises a monofunctional unsaturated acrylic or methacrylic acid ester of a non-tertiary alkyl alcohol wherein the alkyl group of said alcohol contains from 4 to 10 carbon atoms.

7. The composition of claim 5 wherein the at least one acrylic or methacrylic acid ester comprises sec-butyl acrylate, n-butyl acrylate, tert-butyl acrylate, butyl methacrylate, isoamyl acrylate, 2-methylbutyl acrylate, 4-methyl-2-pentyl acrylate, 2-ethylhexyl acrylate, isooctyl acrylate, isononyl acrylate, isodecyl methacrylate, isodecyl acrylate, dodecyl acrylate, tetradecyl acrylate, ethyl acrylate, isobornyl acrylate, or any mixture thereof.

8. The composition of claim 5 wherein the at least one acrylic or methacrylic acid ester comprises isooctyl acrylate or 2-ethylhexyl acrylate.

9. The composition of claim 5 wherein the free radically polymerizable polar comonomer comprises a monoolefinic monocarboxylic acid; a salt of a monoolefinic monocarboxylic acid; a monoolefinic dicarboxylic acid; a salt of a monoolefinic carboxylic acid; an acrylamide; an N-substituted acrylamide; an N-vinyl lactam or any mixture thereof.

10. The composition of claim 5 wherein the free radically polymerizable polar comonomer comprises acrylic acid, methacrylic acid, itaconic acid, crotonic acid, maleic acid, fumaric acid, vinyl acetate, sulfoethyl methacrylate, N-vinyl pyrrolidone, N-vinyl caprolactam, acrylamide, t-butyl acrylamide, dimethylamino ethyl acrylamide, N-octyl acrylamide, hydroxy ethyl acrylate, hydroxy ethyl methacrylate, sodium methacrylate, ammonium acrylate, sodium acrylate, trimethylamine p-vinyl benzimide, N,N-dimethyl-N-(beta-methoxy-ethyl) ammonium propionate betaine, trimethylamine methacrylamide, 1,1-dimethyl-1-(2,3-dihydroxypropyl)amine methacrylamide or any mixture thereof.

11. The composition of claim 5 wherein the free radically polymerizable polar comonomer comprises acrylic acid.

12. The composition of claim 4 wherein the acrylate polymer comprises a copolymer of isooctyl acrylate and acrylic acid.

13. The composition of claim 1 wherein the softening agent comprises a terpene; an alcohol containing from 8 to 36 carbon atoms; a fatty acid, fatty acid ester or fatty acid amide having from 8 to 36 carbon atoms; a glyceride of a fatty acid having from 8 to 36 carbon atoms; an alkyl pyrrolidone carboxylate wherein the alkyl group contains from 6 to 36 carbon atoms or any mixture thereof.

14. The composition of claim 1 wherein the softening agent comprises terpineol, isopropyl myristate, or a mixture thereof.

15. The composition of claim 1 wherein the drug is incorporated within the microspheres.

16. The composition of claim 1 wherein the drug comprises a steroid.

17. The composition of claim 16 wherein the drug comprises a combination of steroids.

18. The composition of claim 17 wherein the drug comprises a combination of an estrogen and a progestin.

19. The composition of claim 1 wherein the drug comprises testosterone or levonorgestrel.

20. A transdermal drug delivery device comprising the transdermal drug delivery composition of claim 1 disposed upon a backing.

21. A method of preparing a transdermal drug delivery composition comprising the steps of:

forming an oil phase comprising one or more acrylic acid ester, methacrylic acid ester, or vinyl ester monomers alone or in any combination; a non-reactive, oil soluble softening agent and/or drug; and an oil soluble free radical initiator in an aqueous phase comprising an aqueous medium comprising at least one suspension stabilizer or surfactant and b) initiating polymerization of the oil phase in the aqueous phase, thereby forming an adhesive microsphere transdermal drug delivery composition.

22. A method of preparing a transdermal drug delivery composition of claim 21, wherein the polymeric microspheres are inherently tacky.

* * * * *

UNITED STATES PATENT AND TRADEMARK OFFICE
CERTIFICATE OF CORRECTION

PATENT NO. : 6,312,715 B1
DATED : November 6, 2001
INVENTOR(S) : Cantor, Adam S.

It is certified that error appears in the above-identified patent and that said Letters Patent is hereby corrected as shown below:

<u>Title page,</u>
Item [75], after "St. Paul" insert -- , MN --;
After "Woodbury" insert -- , MN --;
After "St. Paul" insert -- , MN --;
After "Arcadia" insert -- , CA --;
After "Maplewood" insert -- , MN --;
Delete ", all of MN (US)" and insert in place thereof -- all of (US) --.

<u>Column 8,</u>
Line 6, delete the word "thereof" and insert in place thereof -- thereof. --;
Line 30, delete the word "bomeol," and insert in place thereof -- borneol --.

<u>Column 11,</u>
Line 35, delete "and is" and insert in place thereof -- and $f$ is --;
Line 37, delete the word "fain" and insert in place thereof -- $f$ in --.

<u>Column 13,</u>
Line 27, delete the word "system" and insert in place thereof -- systems --.

<u>Column 14,</u>
Table 3, Line 59, delete "29" and insert in place thereof -- 20 --.

<u>Column 15,</u>
Line 37, delete "and d" and insert in place thereof -- and --;
Line 56, delete "the" and insert in place thereof -- The --.

<u>Column 19,</u>
Line 16, delete the word "reactor" and insert in place thereof -- deionized --;
Line 17, after "The" insert the words -- reactor was --.

UNITED STATES PATENT AND TRADEMARK OFFICE
CERTIFICATE OF CORRECTION

PATENT NO.     : 6,312,715 B1
DATED          : November 6, 2001
INVENTOR(S)    : Cantor, Adam S.

It is certified that error appears in the above-identified patent and that said Letters Patent is hereby corrected as shown below:

Column 22,
Line 3, delete the word "forming" and insert in place thereof -- a) forming --.

Signed and Sealed this

Twenty-ninth Day of October, 2002

Attest:

Attesting Officer

JAMES E. ROGAN
*Director of the United States Patent and Trademark Office*